United States Patent [19]
Bertin

[11] Patent Number: 6,080,196
[45] Date of Patent: Jun. 27, 2000

[54] PATELLA HEIGHT GAUGE AND METHOD OF LOCATING A PATELLA USING SAME

[76] Inventor: Kim C. Bertin, 1879 Ridge Hollow Dr., Bountiful, Utah 84010

[21] Appl. No.: 09/262,543

[22] Filed: Mar. 4, 1999

[51] Int. Cl.[7] ............................... A61F 2/38; A61B 17/58
[52] U.S. Cl. ....................................... 623/20.14; 606/102
[58] Field of Search ................. 606/79, 102; 128/898; 623/18, 20

[56] References Cited

U.S. PATENT DOCUMENTS

| | | | |
|---|---|---|---|
| 4,364,389 | 12/1982 | Keller | 606/86 |
| 4,736,737 | 4/1988 | Fargie et al. | 606/88 |
| 5,326,363 | 7/1994 | Alkins | 623/20 |
| 5,417,693 | 5/1995 | Sowden et al. | 606/85 |
| 5,520,692 | 5/1996 | Ferrante | 606/80 |
| 5,549,683 | 8/1996 | Bonutti | 623/20 |
| 5,571,197 | 11/1996 | Insall | 623/20 |
| 5,683,396 | 11/1997 | Tokish et al. | 606/87 |
| 5,702,401 | 12/1997 | Shaffer | 606/102 |
| 5,702,460 | 12/1997 | Carls et al. | 623/20 |
| 5,735,904 | 4/1998 | Pappas | 623/20 |
| 5,782,924 | 7/1998 | Johnson | 623/20 |
| 5,941,884 | 8/1999 | Corvelli et al. | 606/88 |
| 5,951,562 | 9/1999 | Masini | 606/86 |

FOREIGN PATENT DOCUMENTS

WO87/02883  5/1987  WIPO ......................... 606/102

*Primary Examiner*—Paul J. Hirsch
*Assistant Examiner*—Michael B. Priddy
*Attorney, Agent, or Firm*—Todd A. Dawson

[57] ABSTRACT

A provisional knee implant assembly includes a femoral provisional having an articulating surface and a plurality of locating openings. A patella height gauge has at least two projections which each engage with a corresponding locating opening in the femoral provisional. The patella height gauge includes at least one visual locating reference for a patella. The femoral provisional is located relative to the patella by placing the femoral provisional on a distal end of the femur; attaching the patella height gauge to the femoral provisional; overlying the patella onto the gauge; and repositioning the femoral provisional relative to the one or more visual locating references on the patella height gauge.

13 Claims, 1 Drawing Sheet

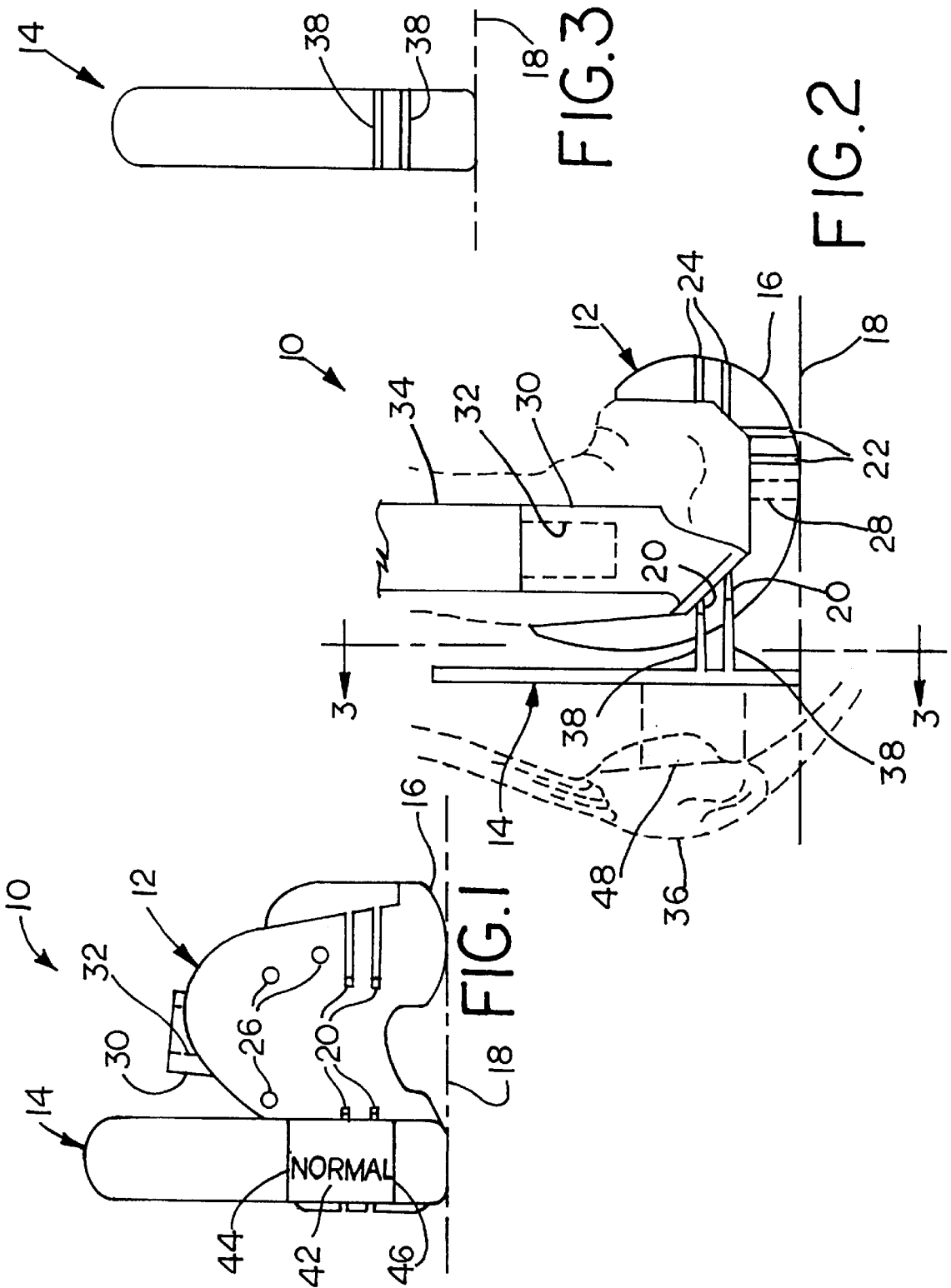

PATELLA HEIGHT GAUGE AND METHOD OF LOCATING A PATELLA USING SAME

BACKGROUND OF THE INVENTION

1. Field of the Invention

The present invention relates to orthopaedic implants, and, more particularly, to provisional implants used to check, align, mark, cut, etc. various surfaces on a bone.

2. Description of the Related Art

During a revision knee surgery, the primary implant is removed from the distal end of a femur and a revision implant is replaced on the distal end of the femur. A provisional implant is commonly used during revision surgery after the old primary implant is removed to provide a visual indication to the surgeon that the new primary implant will properly fit the reshaped bone and function properly. Since many of the anatomical landmarks which are present during a primary surgery no longer exist during a revision surgery, the provisional allows a surgeon to visually orient and align the implant. The provisional implant performs the dual function of a cutting guide and, therefore, may include a plurality of bone pin openings, saw guides, and/or threaded openings allowing attachment to and shaping of the distal end of the femur.

It is advantageous to align the joint line between the new femoral component and tibial component with the patella implant, since in many cases the patella is the only anatomical landmark that remains after the primary implant is removed. It is known that the patella implant may be located relative to the joint line defined by the articulating surface of the provisional implant so that the patella implant properly interfaces with the revision implant. Typically, a surgeon simply estimates the femoral and tibial component location relative to the patella or preforms a trial reduction to visually determine if the placement of the components is correct relative to the patella. Placement of the femoral and tibial components relative to the patella implant is subject to parallax and alignment errors by the surgeon, and is inconsistent, which may lead to a less than optimal performance of the prosthetic knee after implantation.

What is needed in the art is a surgical technique using orthopaedic instrumentation which consistently and accurately allows a femoral provisional component to be located relative to the patella.

SUMMARY OF THE INVENTION

The present invention provides a patella height gauge which connects to a provisional femoral implant and includes a visual locating reference for indicating to the surgeon the relative position of the femoral component and the patella.

The invention comprises, in one form thereof, a provisional knee implant assembly including a femoral provisional having an articulating surface and a plurality of locating openings. A patella height gauge has at least two projections which each engage within a corresponding locating opening in the femoral provisional. The patella height gauge includes at least one visual locating reference for a patella.

The invention comprises, in another form thereof, a method of locating a femoral provisional implant relative to a patella in a knee. The method includes the steps of: placing a provisional on an end of a bone at the knee; attaching a patella height gauge to the provisional; and adjusting the position of the femoral component relative to the bone to locate the patella relative to at least one visual locating reference on the patella height gauge.

An advantage of the present invention is that the femoral component patella can be quickly, easily, and accurately located relative to a joint line of the knee as indicated by the patella.

Yet other objects of the invention will become apparent upon a reading of the following description taken with the accompanying drawings.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a front view of a femoral provisional with an embodiment of a patella height gauge of the present invention attached therewith;

FIG. 2 is a side view of the femoral provisional and patella height gauge of FIG. 1, relative to a femur and patella; and FIG. 3 is another side view of the patella height gauge shown in FIGS. 1 and 2.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, there is shown an embodiment of a provisional knee implant assembly 10 of the present invention which generally includes a provisional 12 and a patella height gauge 14.

Provisional 12 is in the form of a femoral provisional which is temporarily affixed to the distal end of a femur 13 at the knee joint to mark, align, cut, etc., the distal end of femur 13 for subsequent implantation with a revision implant. Provisional 12 includes an articulating surface 16 which defines a joint line 18 with an articulating surface of a tibial implant (not shown).

Provisional 12 also includes a plurality of locating openings which are used to receive other devices or instrumentation, in known manner. For example, provisional 12 includes locating openings in the form of saw guides 20, 22, and 24, bone pin openings 26 and threaded openings 28. Provisional 12 also includes a stem base 30 with a cylindrical opening 32 which is internally threaded and allows attachment with a provisional stem, such as a straight stem 34 or offset stem (not shown).

Patella height gauge 14 is connected with provisional 12 and allows provisional 12 to be adjusted relative to patella 36. More particularly, patella height gauge 14 includes a visual locating reference represented by the area labeled "NORMAL" between the visual lines 44 and 46 which corresponds to the limits of the patella 36.

More specifically, patella height gauge 14 includes a pair of projections 38 which extend into and engage with a corresponding pair of saw guides 20 on either the medial side or lateral side of provisional 12. Projections 38 each include a tapered end which provide a wedge-like interference fit within saw guides 20. When projections 38 are pressed into saw guides 20, patella height gauge 14 remains in place until manually removed.

Area 42 between visual lines 44 and 46 is positioned relative to joint line 18 defined by patella 36 such that the articulating surface of the provisional implant 12 is proper relative to the joint line. In the embodiment shown, line 46 is located a distance of 10 millimeters from joint line 18; line 44 is located a distance of 30 millimeters from joint line 18; and area 42 spans a distance of 20 millimeters extending between visual lines 44 and 46.

During revision surgery, a primary implant is removed from femur 13 and provisional implant 12 is placed on the distal end of femur 13. Provisional 12 may be temporarily attached to femur 13 using pins passing through bone pin openings 26, if desirable. Patella height gauge 14 is then attached with provisional 12 by inserting projections 38 into a pair of saw guides 20 on an anterior side of provisional 12. The patella, with tendons attached, is then placed back into its normal position and overlying the patella height gauge 14. In this position, the surgeon can use the marking on the height gauge to reposition the femoral provisional implant on the bone relative to the joint line as determined by the patella.

In the embodiment shown, patella height gauge 14 includes a pair of projections 38 which engage with corresponding saw guides 20, as described above. However, it will also be appreciated that patella height gauge 14 may be differently configured to attach with provisional 12. For example, patella height gauge 14 may include a single projection which engages with a saw guide 20, or a plurality of projections which engage with bone pin openings 26 and/or saw guides 20.

In the embodiment of patella height gauge 14 shown in the drawings, the visual locating reference is in the form of two visual lines 44 and 46 as described above. However, it is also to be appreciated that patella height gauge 14 may include one or more visual locating references other than visual lines. For example, patella height gauge 14 may include one or more projections which allow a surgeon to locate an area to be cut on patella 36 for receiving a patella implant.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A provisional knee implant assembly, comprising:
 a femoral provisional including an articulating surface and a plurality of locating openings;
 a patella height gauge having at least two projections which each engage with a corresponding one of said locating opening in said femoral provisional, said patella height gauge including at least one visual locating reference for a patella.

2. The provisional knee implant assembly of claim 1, wherein said plurality of locating openings comprise one of saw guides, bone pin openings, and threaded openings.

3. The provisional knee implant assembly of claim 2, wherein each of said plurality of locating openings comprises a saw guide.

4. The provisional knee implant assembly of claim 3, wherein said patella height gauge includes a pair of projections which respectively engage with two of said saw guides.

5. The provisional knee implant assembly of claim 4, wherein said two saw guides are located on an anterior side of said femoral provisional.

6. The provisional knee implant assembly of claim 1, wherein said at least one visual locating reference comprises at least one visual line on said patella height gauge.

7. The provisional knee implant assembly of claim 6, wherein said articulating surface on said femoral provisional defines a joint line, and wherein said at least one visual line provides a visual locating reference for the patella relative to said joint line.

8. The provisional knee implant assembly of claim 1, wherein said at least one visual locating reference comprises two visual lines on said patella height gauge.

9. The provisional knee implant assembly of claim 8, wherein said articulating surface on said femoral provisional defines a joint line, and wherein said two visual lines provide a visual locating reference for the patella relative to said joint line.

10. A method of locating a femoral provisional implant in a knee, comprising the steps of:
 placing a femoral provisional implant on an end of a bone at the knee;
 attaching a patella height gauge to said femoral provisional implant; and shifting the femoral provisional implant on the end of the bone relative to at least one visual locating reference on said patella height gauge, wherein said femoral provisional implant includes a plurality of openings and wherein said attaching step comprises engaging at least two projections on said patella height gauge within corresponding locating openings in said femoral provisional implant.

11. The method of claim 10, wherein said placing step comprises placing said femoral provisional at a distal end of a femur.

12. A provisional knee implant assembly, comprising:
 a femoral provisional knee implant including an articulating surface defining a joint line; and
 a patella height gauge connected with said femoral provisional knee implant, said patella height gauge including at least one visual locating reference for a patella, each said visual locating reference being positioned a predetermined distance from said joint line.

13. The provisional knee implant assembly of claim 12, wherein said at least one visual locating reference comprises a pair of visual lines.

* * * * *